United States Patent [19]
Koeda et al.

[11] Patent Number: 5,319,954
[45] Date of Patent: Jun. 14, 1994

[54] APPARATUS FOR DETECTING BUBBLES IN REAGENT PIPETTING APPARATUS

[75] Inventors: Noriaki Koeda; Takayoshi Izumi, both of Kobe; Kunio Tanaka, Kakogawashi, all of Japan

[73] Assignee: Toa Medical Electronics Co., Ltd., Kobe, Japan

[21] Appl. No.: 897,851

[22] Filed: Jun. 12, 1992

[30] Foreign Application Priority Data

Aug. 1, 1991 [JP] Japan .................................. 3-68304

[51] Int. Cl.$^5$ ............................................ G01N 7/00
[52] U.S. Cl. ............................................... 73/19.1
[58] Field of Search .......................... 73/19.01, 19.1; 137/386, 393

[56] References Cited

U.S. PATENT DOCUMENTS

| | | | |
|---|---|---|---|
| 3,470,902 | 10/1969 | Hackman | 137/386 |
| 3,681,546 | 8/1972 | Coin et al. | 137/386 |
| 4,235,095 | 11/1980 | Liebermann | 73/19.1 |
| 4,444,222 | 4/1984 | Yamagiwa | 137/393 |
| 4,696,191 | 9/1987 | Claytor et al. | 73/19.01 |
| 4,772,157 | 9/1988 | Obermeyer | 137/386 |
| 5,152,175 | 10/1992 | Reynolds | 73/19.01 |

*Primary Examiner*—Hezron E. Williams
*Assistant Examiner*—Valerie D. Francies
*Attorney, Agent, or Firm*—Jones, Tullar & Cooper

[57] ABSTRACT

In an automatic analyzer of samples, the liquid specimen and the reagent are mixed in a reaction container to react. If, however, there is a bubble in the reagent container, a accurate amount of a reagent may not be dispensed. Accordingly, a liquid surface detecting circuit for detecting the liquid surface on the basis of the impedance change between a pipet and a ground is disposed, and the height of the liquid surface before and after suction of the reagent is compared on the basis of the liquid surface detecting information, and the bubble is detected when the difference is more than a specified value, and accordingly the driving circuit of the driving source is controlled by the control circuit. Thus, when dispensing the reagent in the reagent container by a pipet, the bubble can be detected securely and accurately, and this apparatus may be used in a slender reagent container.

1 Claim, 3 Drawing Sheets

5,319,954

APPARATUS FOR DETECTING BUBBLES IN REAGENT PIPETTING APPARATUS

BACKGROUND OF THE INVENTION

The invention relates to an apparatus for detecting air bubbles formed at the time of pipetting reagents in an apparatus for analyzing liquid specimens automatically, or more particularly to an apparatus for detecting bubbles, formed also in a slender reagent container, by securely detecting bubbles when dispensing reagent in a reagent container by means of a pipet (pipette).

In an automatic analyzer, various reagents are used. The reagent in the reagent container is dispensed by a specific amount from the pipet connected to a measuring device such as a syringe, and is discharged into the reaction container. In the reaction container, the specimen and reagent are mixed, and they react with each other.

Bubbles may be formed in the reagent, and if bubbles are formed in the reagent container, a correct amount of reagent may not be obtained. For example, when the reagent container is turned upside down and agitating to thaw the frozen reagent, or when conveying or transporting of a reagent, bubbles are formed. In the case of a reagent containing a component that easily forms bubbles, the bubbles do not break and remain floating on the liquid surface.

On the other hand, in order to avoid deposit of reagent on the outer wall of the pipet, a pipet having a liquid level detecting function is used. When detecting the liquid level, if bubbles are present, the bubble surface may be mistaken for the liquid surface, and accurate dispensing is not possible.

The Japanese examined Patent Hei. 1-45870, (the Japanese Laid-open Patent Sho. 58-154664) discloses a liquid weighing amount confirmation control device for confirming the liquid sampling amount by the pipet by comparing the liquid level height in the container and lower extent of the pipet. In this device, when the difference of the two is more than ±10 to 20%, it is regarded to be clogging.

The Japanese Laid-open Patent Hei. 2-40562 discloses a liquid dispensing device for detecting the liquid surface before and after dispensing and for monitoring improper dispensing. It is also proposed to regard the liquid surface detecting position after dispensing in the previous step as the liquid surface detecting position before dispensing of the succeeding step.

In both the device of 1-45870 and the device of 2-40562, the liquid surface detecting means (or level sensor) is installed near the pipet, but separately from the pipet, and is inserted into the container together with the pipet so as to detect the liquid surface.

Accordingly, such structure cannot be applied in a reagent container. This is a serious problem because the trend toward downsizing is particularly accelerated recently. When the reagent container is not so slender, but if the reaction container is slender, the result is the same, that is, a slender suction part is needed.

Besides, since the liquid surface detecting position and liquid sucking (aspirating) position are different, it is difficult to detect bubbles. This point will be explained with the aid of FIG. 1. When the pipet 40 and liquid surface detecting means 41 descend and there is a bubble 42 just beneath the liquid surface detecting means 41, the liquid surface detecting means 41 detects the bubble 42 as the liquid surface 44, thereby stopping the descending motion of the pipet 40 and liquid surface detecting means 41. Since the pipet 40 does not reach the liquid surface, the reagent cannot be sucked correctly. If, for example, the reagent container diameter is 12 mm and the reagent dispensing amount is 10 $\mu$l, the liquid surface moving amount is not more than 0.1 mm, and the difference in such a small movement cannot be detected easily.

OBJECT AND SUMMARY OF THE INVENTION

It is hence a primary object of the present invention to provide an apparatus for detecting bubbles in a reagent pipetting apparatus, which is simple in structure, applicable in a slender container, and capable of securely detecting bubbles in a container.

To achieve the above object, the present invention provides an apparatus for detecting bubbles in reagent pipetting apparatus comprising:

a pipet for sucking and dispensing a reagent which pipet is moved up and down by a driving source, a driving circuit for driving and controlling the driving source, a liquid surface detecting circuit for detecting the liquid surface on the basis of the impedance change between pipet and the ground, and a control circuit for comparing the height of the liquid surface before and after suction of the reagent on the basis of the liquid surface detecting information of the liquid surface detecting circuit, detecting a bubble when the difference is more than a specific value, and thereby controlling the driving circuit.

In this way, by using the liquid surface detecting circuit for detecting the liquid surface on the basis of the impedance change between the front end of the pipet and the ground, the changing amount of the liquid surface is detected, and when the change is greater than usual, the bubble is detected.

DETAILED DESCRIPTION OF THE PREFERRED EMBODIMENTS

Figure 1:
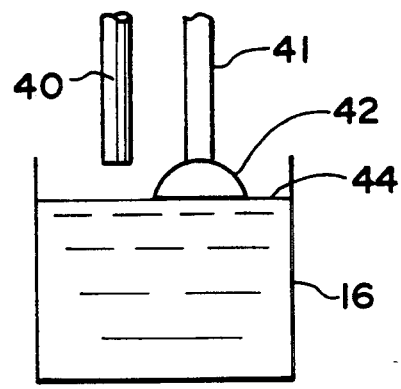
FIG. 1 is an explanatory diagram showing the state of detecting a bubble in a conventional apparatus.

Referring now to the drawings, some of the preferred embodiments of the invention are described in detail below.

Figure 2:
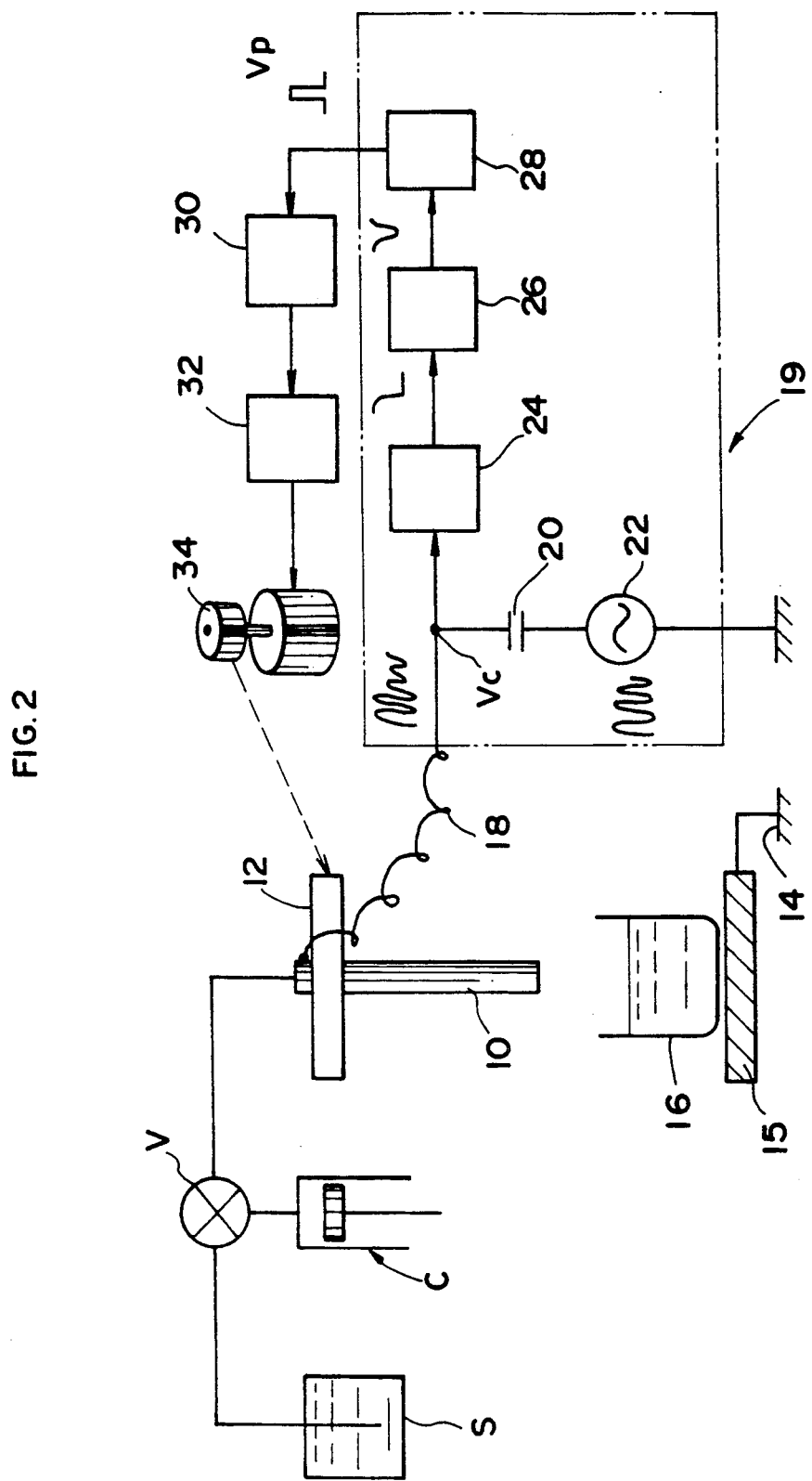
FIG. 2 is a schematic diagram of an apparatus for detecting bubbles in a reagent pipetting apparatus according to an embodiment of the present invention.

The present invention relates to, as shown in FIG. 2, an apparatus for detecting bubbles in reagent pipetting apparatus comprising:

a pipet 10 for sucking and dispensing a reagent the pipet 10 is moved up and down by a driving source 34, a driving circuit 32 for driving and controlling the driving source 34, a liquid surface detecting circuit 19 for detecting the liquid surface on the basis of the impedance change between pipet 10 and the ground 14, and a control circuit 30 for comparing the height of the liquid surface before and after suction of the reagent on the basis of the liquid surface detecting information of the liquid surface detecting circuit 19, detecting a bubble when the difference is more than a specific value, and thereby controlling the driving circuit 32.

In this way, by using the liquid surface detecting circuit 19 for detecting the liquid surface on the basis of the impedance change between the front end of the pipet 10 and ground 14, the changing amount of liquid surface is detected, and when the change is greater than usual, a bubble is detected.

FIG. 2 shows an embodiment of the present invention. In FIG. 2, numeral 10 is a pipet, for sucking and dispensing a reagent. The pipet 10 is made of conductive material, such as stainless steel. Numeral 12 is an arm for fixing the pipet 10, and the arm 12 and pipet 10 are designed to be moved up and down together by a driving source 34. Numeral 32 denotes a driving circuit for driving and controlling the driving source 34. Numeral 16 is a reagent container filled with a reagent, and it is put on a stand 15 made of a conductive material grounded to ground 14.

The pipet 10 is connected to the liquid surface detecting circuit 19 through a cable 18. The liquid surface detecting device 19 comprises, for example, a circuit matching capacitor 20, a high frequency oscillator 22 (with an oscillation frequency of, for example, several MHz), a detecting circuit 24, a differential circuit 26, and a comparator circuit 28. Between the liquid surface detecting device 19 and the driving circuit 32, a control circuit 30 is disposed. V is a changeover valve, C is a weighing device, and S is a cleaning liquid tank filled with cleaning liquid.

The technology for detecting the liquid surface on the basis of capacitance change is known hitherto and is explained only briefly below.

Basically, the capacitance between the pipet 10 and ground 14 consists of the composite capacitance of three capacitances, that is, the capacitance $C1$ between the specimen and ground, the capacitance $C2$ between the specimen and the pipet, and the capacitance $C3$ between the pipet and ground, and the total capacitance $Ct1$ is expressed as $$Ct1 = C3 + C1 \cdot C2/(C1+C2)$$

When the pipet 10 comes in contact with the liquid surface, $C2$ becomes $\infty$, and hence the total changes to $$Ct2 = C3 + C1$$

At this time, the amount of change is $$Ct2 - Ct1 = C1^2/(C1+C2)$$

Hence the capacitance increases.

The value of $C1$ varies with the container material, distance from ground, electric conductivity of the specimen, and other conditions. In actual measurement, the amount of change in a plastic container was about 1 to 2 pF.

When a conductive container is used, the resistance change is greater than the capacitance change. Considering this point, in this Specification, "capacitance change" is mentioned as "impedance change".

As the pipet 10 descends to contact with liquid surface, the capacitance between the pipet 10 and the ground 14 increases, and the wave crest value of the detected high frequency signal Vc becomes smaller. This high frequency signal Vc is detected in the detecting circuit 24 and is converted into a DC signal, and further the level change of the DC signal is detected by the differential circuit 26, and it is compared with a specific level in the comparator circuit 28, thereby obtaining a liquid surface detecting signal Vp.

By the liquid surface detecting signal Vp, the driving circuit 30 stops the descending motion of the pipet 10 through the driving circuit 32 and driving source 34, thereby detecting the bubble.

Figure 3:
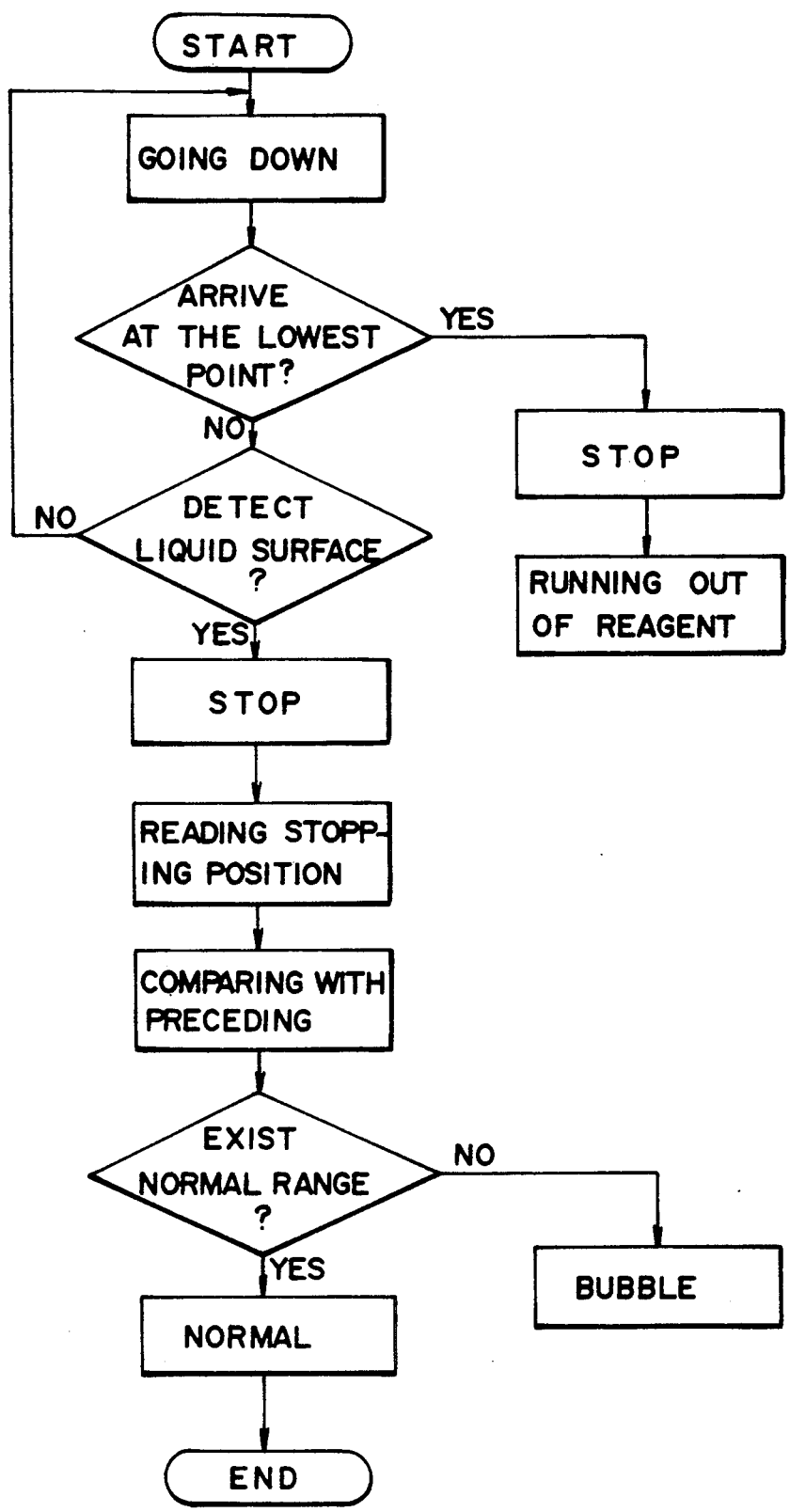
FIG. 3 is a processing flow chart for the control circuit in FIG. 2.

FIG. 3 is a processing flow chart 20 the control circuit 30. The pipet 10 is initially located at the initial position shown in FIG. 2. By a descending command, it begins to descend. Whether the pipet 10, reaches the lowest point or not is detected by a limit switch (not shown). If the lowest point is reached before arriving at the liquid surface, the descending motion is stopped, and a reagent shortage alarm is issued. If the liquid surface is detected before reaching the lowest point, the descending motion is stopped, and the stopping position is read. The driving source 34 is a stepping motor which rotates by an angle proportional to, for example, a given number of pulses, and by counting the number of pulses from the start of driving, the distance from the initial position to the liquid surface is known.

In the memory (not shown) of the control circuit 32, the position of the liquid surface obtained by previous measurement is stored, and it is compared with the present position, and the difference is judged to be within a specified range or not. If within the specified range, it is judged normal, and if out of the specified range, it is judged to be a bubble. In the case where it is judged to be a bubble, an alarm is issued.

Figure 4:
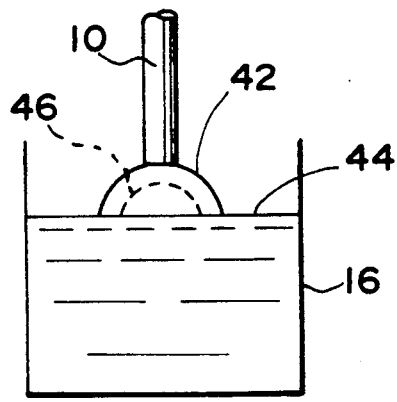
FIG. 4 is an explanatory diagram showing the state of detecting a bubble in the apparatus of the present invention.

In the apparatus of the present invention, too, if there is a bubble, the bubble is detected as a liquid surface, and hence the reagent cannot be sucked accurately. Air is sucked. Therefore, the bubble must be detected. And in case of the detection of the bubble, an alarm is given. As shown in FIG. 4, if the bubble 42 is detected, the bubble 42 becomes a smaller bubble 46 by suction (aspiration) as indicated by the broken line. If the suction amount is very slight, it is possible to suck a reagent by the action of the surface tension of the reagent, without having to suck a reagent while lowering the pipet. Since the volume of a bubble is smaller than the volume of the container 16, for example, even in a very slight suction of 10 µl, the height of the bubble results in a difference large enough to be detected. Or, when the pipet descends next time, the bubble might have been moved. Accordingly, if the liquid surface detecting position is too low as compared with the liquid surface detecting position of the previous time (the number of pulses for driving the motor is too large), it is judged to be a bubble. And the previous stopping position is corrected by the changing volume of the liquid reagent surface calculated from the previous sucking reagent volume. As a result, the present stopping position can be estimated. When the present (actual) stopping position is lower than the estimated stopping position over the allowable error, it is judged that the previous suction is the suction of a bubble.

To the contrary, the liquid surface might be accurately detected the previous time, and the bubble may be detected this time. Hence, if the liquid surface detecting position is high as compared with the liquid surface detecting position of the previous measurement (the number of pulses for driving the motor is small), it may be also judged to be a bubble. Because the present (actual) stopping position is higher than the estimated stopping position over the allowable error, it is judged that the present stopping is the stopping by a bubble.

Thus, it is judged to be normal in a range of $P1 < \Delta L < P2$, and to be a bubble, if out of this range, where $\Delta L$ is the difference of (present number of driving pulses)−(previous number of driving pulses), and P1 and P2 may be any values suited to the purpose.

Being thus constructed, the present invention brings about the following effects:

(1) Since the liquid surface detecting means is not disposed aside from the pipet, it is usable in a slender reagent container, and it is suited to a liquid specimen analyzing system treating a small quantity of a reagent.

(2) The bubble can be detected securely and accurately.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claim.

What is claimed is:

1. An apparatus for detecting bubbles in reagent pipetting apparatus comprising:
    a pipet for sucking and dispensing a reagent which is moved up and down by a driving source;
    a driving circuit for driving and controlling the driving source;
    a liquid surface detecting circuit connected to the pipet for detecting the liquid surface on the basis of the impedance change between the pipet and a ground; and
    a control circuit connected to the liquid surface detecting circuit and the driving circuit for comparing the height of the liquid surface before and after suction of the reagent on the basis of the liquid surface detecting information of the liquid surface detecting circuit, detecting a bubble when the difference is more than a specific value, and thereby controlling the driving circuit.

* * * * *